(12) United States Patent
Zhang et al.

(10) Patent No.: US 10,472,355 B2
(45) Date of Patent: Nov. 12, 2019

(54) CANCER TREATMENT UTILIZING SP-141 TO BIND WITH MDM2 AND ACT AS AN INHIBITOR OF MDM2 EXPRESSION

(71) Applicant: Texas Tech University System, Lubbock, TX (US)

(72) Inventors: Ruiwen Zhang, Amarillo, TX (US); Wei Wang, Amarillo, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/513,882

(22) PCT Filed: Sep. 25, 2015

(86) PCT No.: PCT/US2015/052216
§ 371 (c)(1),
(2) Date: Mar. 23, 2017

(87) PCT Pub. No.: WO2016/049453
PCT Pub. Date: Mar. 31, 2016

(65) Prior Publication Data
US 2017/0283413 A1 Oct. 5, 2017

Related U.S. Application Data

(60) Provisional application No. 62/055,796, filed on Sep. 26, 2014.

(51) Int. Cl.
*C07D 471/04* (2006.01)
(52) U.S. Cl.
CPC .................. *C07D 471/04* (2013.01)
(58) Field of Classification Search
CPC .................................................... C07D 471/04
USPC .......................................................... 546/86
See application file for complete search history.

(56) References Cited

U.S. PATENT DOCUMENTS 8,329,723 B2 * 12/2012 Buolamwini ........ A61K 31/437
514/292
2008/0306130 A1 12/2008 Weissman et al.
2010/0317667 A1 12/2010 Buolamwini et al.
2013/0131070 A1 5/2013 Buolamwini
2013/0190258 A1 7/2013 Cashman et al.
2014/0179877 A1 * 6/2014 Nilsson ................ A61K 31/704
525/418

FOREIGN PATENT DOCUMENTS

WO WO-2010123583 A2 * 10/2010 ........... A61K 31/437
WO 2014123882 A1 8/2014

OTHER PUBLICATIONS

Tamara Minko et al Enhancing the anticancer efficasy of Camptothecin using biotinylated poly(ethyleneglycol) conjugates in sensitive and multidrug-resistant human ovarian carcinoma celles., Jun. 2002.*
Vitamin-mediated targeting as a potential mechanism to increase drug uptake by tumours, Gregory Russell-Jones et al, Sep. 2004.*
Tripodo Giuseppe et al, New Prespective in Cancer Therapy: The Biotin-Antitumor Molecules conjugates, Apr. 23, 2014.*
Wang, W. et al., The pyrido[b]indole MDM2 inhibitor SP-141 exerts potent therapeutic effects in breast cancer models, Nature Communications (2014) 5:5086, 12 pages.
Nag, S. et al., A quantitative LC-MS/MS method for determination of SP-141, a novel pyrido[b]indole anticancer agent, and its application to a mouse PK study, Journal of Chromatograph B (2014) 969:235-240.
Wang, W. et al., Identification of a New Class of MDM2 Inhibitor That Inhibits Growth of Orthotopic Pancreatic Tumors in Mice, Gastroenterology (2014) 147:893-902.
Nag, S. et al., Development and validation of a rapid HPLC method for quantitation of SP-141, a novel pyrido[b]indole anticancer agent, and an initial pharmacokinetic study in mice, Biomedical Chromatography (2015) 29:654-663.
Qin, J.-J. et al., Oral delivery of anti-MDM2 inhibitor SP141-loaded FcRn-targeted nanoparticles to treat breast cancer and metastasis, Journal of Controlled Release (2016) 237:101-114.

* cited by examiner

*Primary Examiner* — Rita J Desai
(74) *Attorney, Agent, or Firm* — Kevin L. Soules; Kermit D. Lopez; Luis M. Ortiz

(57) ABSTRACT

An SP-141 compound is a novel small molecule that can serve as a molecular-targeted chemotherapeutic agent. In one embodiment, the labeled compound can comprise SP-141, which comprises 6-methoxy-1-(naphthalen-1-yl)-9 H-pyrido[3,4-b]indote. The compound inhibits expression of oncogenes such as the Mouse Double Minute 2 protein. The compound can bind directly to Mouse Double Minute 2 to inhibit cancer growth including breast cancer growth.

1 Claim, 30 Drawing Sheets

SP-141

Biotin–SP-141

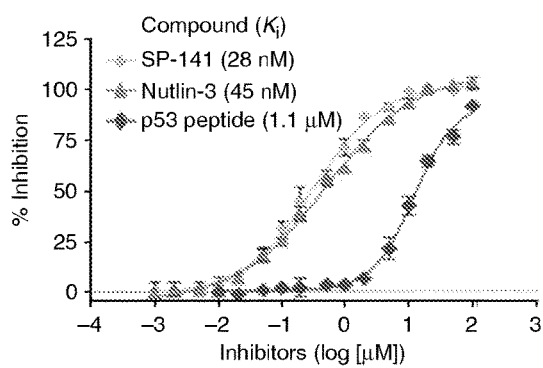
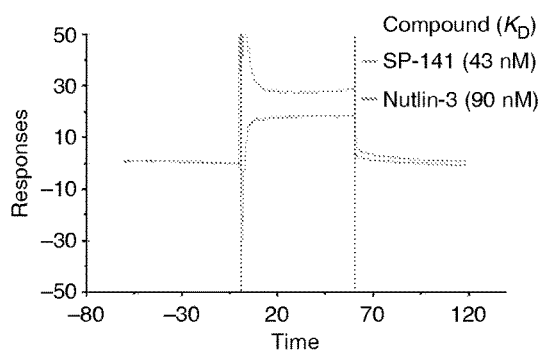
FIG. 7A
FIG. 7B

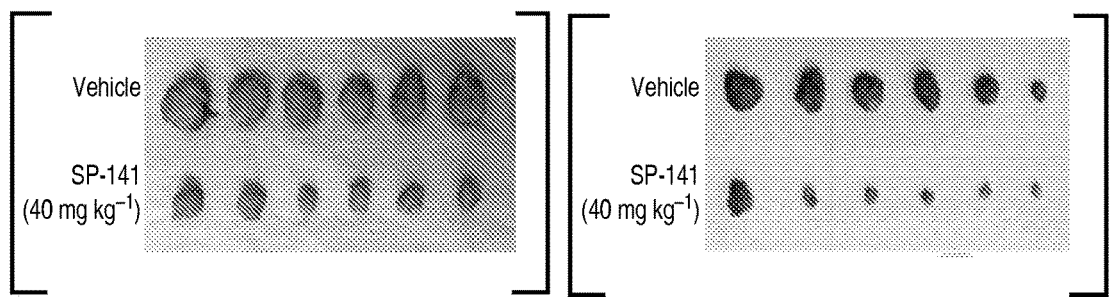
FIG. 14A                    FIG. 14B

CANCER TREATMENT UTILIZING SP-141 TO BIND WITH MDM2 AND ACT AS AN INHIBITOR OF MDM2 EXPRESSION

CROSS REFERENCE TO RELATED APPLICATIONS

This application is the US national phase of International Application No. PCT/US2015/052216, filed on Sep. 25, 2015 under the PCT (Patent Cooperation Treaty), and claims priority to U.S. Provisional Patent Application. No. 62/055,796, filed Sep. 26, 2014. The entire contents of these applications are incorporated herein by reference.

STATEMENT OF GOVERNMENT RIGHTS

This invention was developed under a commercialization agreement between the Texas Tech University System and National Institutes of Health (NIH) under Contract No. R01 CA186662 DE-AC04-94AL85000 and also with the American Cancer Society (ACS) under Contract No. RSG-15-009-01-CDD.

TECHNICAL FIELD

Embodiments are related to cancer treatment. More particularly, embodiments are directed to the utilization of SP-141 to directly bind to MDM2, inhibit MDM2 expression, and induce its autoubiquitination and proteasomal degradation. Embodiments are also related to identifying SP-141 as a lead compound for cancer treatment.

BACKGROUND

Recent advances in breast cancer biology have demonstrated that the loss of tumor suppressors, such as p53, and over-expression of oncogenes, including Mouse Double Minute 2 (MDM2), contribute to the poor response to treatment and poor prognosis in breast cancer patients. The MDM2 oncogene is amplified and over-expressed in a number of human malignancies, including breast cancer. High levels of the MDM2 protein often correlate with decreased survival rates in patients. The MDM2 oncogene is a negative regulator of the tumor suppressor p53, which regulates the cell cycle, maintains the genomic integrity of cells, and controls the cellular response to DNA damage. It also directly binds to p53, represses the transcriptional activity of p53, and promotes p53 degradation. The MDM2 oncoprotein also has p53-independent activities. In addition to inhibiting apoptosis by affecting both pro-apoptotic and anti-apoptotic proteins, MDM2 also alters cell cycle regulation, DNA replication, and DNA repair.

MDM2 oncogene activation has been suggested to be associated with cancer progression and metastasis. Breast cancer is an example where the association has been found. To date, most MDM2 inhibitors have been designed to block the MDM2-p53-binding interphase and have low or no efficacy against advanced cancer with mutant or deficient p53. Furthermore, many treatments cause host toxicity.

Accordingly, there is a need for new anticancer therapies that utilize compounds to bind with MDM2 and inhibit MDM2 expression while minimizing toxicity and promoting anticancer activity independent of p53 status.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

The present inventors have identified SP-141 as a lead compound that can directly bind with MDM2 and inhibit its expression. SP-141 has strong in vitro and in vivo anti-breast cancer activity, with no apparent host toxicity regardless of p53 status.

High-throughput screening and computer-aided, structure-based rational drug design can be used to identify the compound, SP-141, which can directly bind to MDM2, inhibit MDM2 expression, and induce its autoubiquitination and proteasomal degradation.

SP-141 (6-methoxy-1-(naphthalen-1-yl)-9 H-pyrido[3,4-b]indole) shows strong binding to the MDM2 protein and is potent in vitro against several human breast cancer cell lines, regardless of p53 status. It inhibits MDM2 expression and promotes MDM2 autoubiquitination and proteasomal degradation. Furthermore, SP-141 decreases tumor growth and inhibits metastasis in vivo.

It is therefore an aspect of the disclosed embodiments to provide an SP-141 compound comprising a novel small molecule that can serve as a molecular-targeted chemotherapeutic agent. In one embodiment, the compound has the structure shown in FIG. 1. The compound can comprise SP-141 which comprises 6-methoxy-1-(naphthalen-1-yl)-9 H-pyrido[3,4-b]indole. The compound inhibits expression of oncogenes such as the Mouse Double Minute 2 protein. The compound can bind directly to Mouse Double Minute 2 to inhibit cancer growth including breast cancer growth.

BRIEF DESCRIPTION OF THE DRAWINGS

The accompanying figures, in which like reference numerals refer to identical or functionally similar elements throughout the separate views and are incorporated in and form a part of the specification, further illustrate aspects of the embodiments and, together with the background, brief summary, and detailed description, serve to explain the principles of the embodiments.

FIG. 7A illustrates a graph showing the competitive binding to recombinant human MDM2 proteins using FP-based binding assay, in accordance with an example embodiment;

FIG. 7B illustrates a graph showing the competitive KD values of SP-141 to MDM2 as determined using the Biacore assay, in accordance with an example embodiment;

FIG. 14A illustrates a photograph of xenograft tumors treated with SP-141, in accordance with an example embodiment;

FIG. 14B illustrates a photograph of xenograft tumors treated with SP-141, in accordance with an example embodiment;

DETAILED DESCRIPTION

Figure 1:
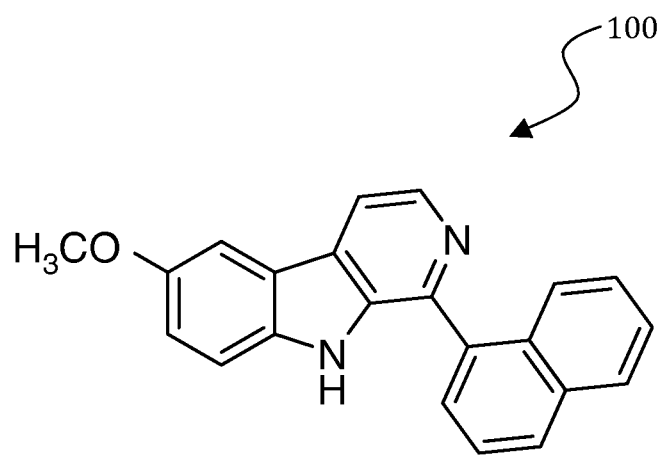
FIG. 1 illustratesthe chemical structure of SP-141 in accordance with an example embodiment.

The following description contains a series of examples wherein previously known unlabeled compounds are processed to yield highly pure labeled compounds that are not previously known.

Example embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The particular values and configurations discussed in the following non-limiting examples can be varied and are cited merely to illustrate one or more embodiments and are not intended to limit the scope thereof.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations. elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms such as "and", "or", or "and/or" as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms, such as "a", "an", or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Breast cancer is the most frequently diagnosed cancer among women in the United States and is the second leading cause of cancer-related death in women. In addition to advanced age, excessive exposure to oestrogens and a deficiency in the maintenance of genomic integrity are two major reasons for high breast cancer risk. Despite an early diagnosis and new treatment options, the mortality rate is still high for patients with advanced breast cancer.

Molecular-targeted therapies, such as selective oestrogen receptor modulators, aromatase inhibitors, and human epidermal growth factor receptor antagonists have been successfully developed and increase survival rates, but have limitations because of intrinsic alternations of multiple molecules or genes at the l genetic and epigenetic levels. In particular, triple-negative breast cancers (TNBC), lacking the expression of the oestrogen receptor (ER), progesterone receptor (PR,) and human epidermal growth factor receptor remain a major cause of breast cancer mortality because of their invasiveness and metastatic potential. These tumors show increased resistance to conventional chemotherapeutic agents.

Oncogene addiction is a phenomenon wherein the survival of cancer cells depends on an activated oncogene. Oncogene addiction has been identified as one of the major mechanisms underlying cancer progression and metastasis. Thus, as described in the embodiments herein, targeting oncogenes has great potential for cancer treatment and prevention. The loss of tumor suppressors, such as p53, and over-expression of oncogenes, including Mouse Double Minute 2 (MDM2), contribute to the poor response to treatment and poor prognosis in breast cancer patients, especially in TNBC. The MDM2 oncogene is amplified and over-expressed in a number of human malignancies, including breast cancer. High levels of the MDM2 protein often correlate with decreased survival in patients.

The MDM2 oncogene is a negative regulator of the tumor suppressor p53, which regulates the cell cycle, maintains the genomic integrity of cells, and controls the cellular response to DNA damage. It also directly binds to p53 and represses the transcriptional activity of p53 and promotes p53 degradation. The MDM2 oncoprotein also has p53-independent activities. In addition to inhibiting apoptosis by affecting both pro-apoptotic and anti-apoptotic proteins, MDM2 also alters cell cycle regulation, DNA replication, and DNA repair.

Animal studies with transgenic mice and clinical observations have established that MDM2 is involved in cancer development and the response to treatment, both dependent and independent of p53. Accordingly, MDM2 can be used as a target for cancer therapy and prevention.

SP-141 is a specific MDM2 inhibitor. By performing high-throughput virtual screening according to the published crystal structures of MDM2, the embodiments herein describe a class of pyrido[b]indole derivatives which have potent binding affinity for the MDM2 protein. On the basis of these core structures. the disclosed embodiments include a series of small molecule MDM2 inhibitors. After cell-based screening, compound SP-141 was found to be the most active.

The embodiments disclosed herein were born from the inventors study of both the in vitro and in vivo antitumor effects of the novel pyrido[b]indole compound disclosed herein, in human breast cancer cell lines. The inventors study resulted in one embodiment of the invention comprising SP-141; a novel computer-designed MDM2 inhibitor that directly targets the MDM2 protein. SP-141 significantly inhibits breast cancer cell growth, but with much lower activity in normal cells, thus providing targeted engagement with cancer cells. SP-141 also reduces the breast cancer cell colony formation, inhibits cell proliferation, induces apoptosis, and arrests cells in the G2/M phase, regardless of their p53 status. SP-141 down regulates MDM2 expression and destabilizes the MDM2 protein by promoting its ubiquitination in vitro, regardless of the p53 status of the cells. SP-141 decreases the growth of tumors, inhibits the MDM2 expression, and modulates the protein levels of various other proteins, with changes similar to those observed in vitro, independent of the p53 status. The inhibition of MDM2 by SP-141 is essential for its antitumor activities. Finally, SP-141 inhibits breast cancer cell migration in vitro and metastasis in vivo. Thus, SP-141 is an effective therapeutic agent that may provide treatment of human breast cancer.

It is important to note that SP-141 exerts its anti-breast cancer activity by directly targeting MDM2, inducing MDM2 degradation, regardless of the p53 status of the cells. This may be achieved without any significant toxicity (as indicated by the histological examination of various tissues and by the body weight changes, in experiments conducted by the inventors in mice). This is remarkable because these studies were performed after 6 weeks of treatment at a relatively high dose of 40 mg!kg, 1 per day. In another embodiment, dosing frequency or formulation optimization may be used to achieve significant anticancer activity at lower doses.

SP-141 specifically binds to the MDM2 protein, as proven by the results from several assays, including the initial molecular docking, biotin avidin pull-down assays, FP-based binding assay, and Biacore assay. Thus. SP-141 significantly decreased the growth of cancer cells with both wild-type (MCF-7) and non-functional p53, as well as oestrogen receptor-dependent (MCF-7) and -independent (MDA-MB-468) cancer cells. SP-141 decreases the growth of both MCF-7 and MDA-MB-468 xenograft tumors. Down regulation of the MDM2 oncoprotein is responsible for the observed cytotoxic effects of SP-141.

In one embodiment, SP-141 can serve as an MDM2 inhibitor. The class of pyrido[b]indole derivatives has potent binding affinity for the MDM2 protein. These core structures can be used to create a series of small molecule MDM2 inhibitors, with compound SP-141 being the most active.

Figure 2:
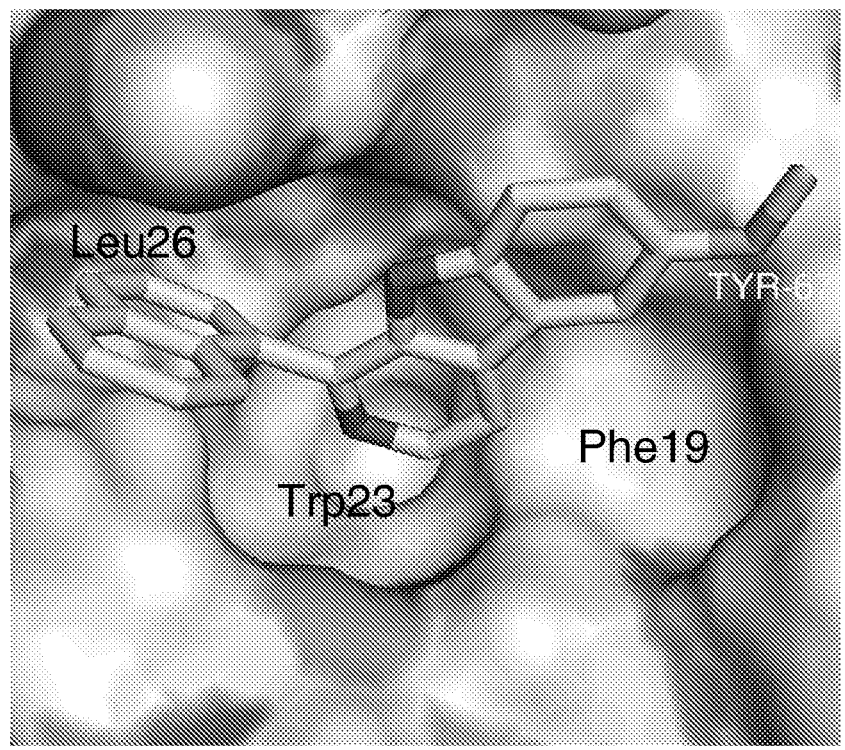
FIG. 2 illustrates the binding site and orientation of SP-141 in the hydrophobic groove of MDM2, in accordance with an example embodiment.
Figure 3:
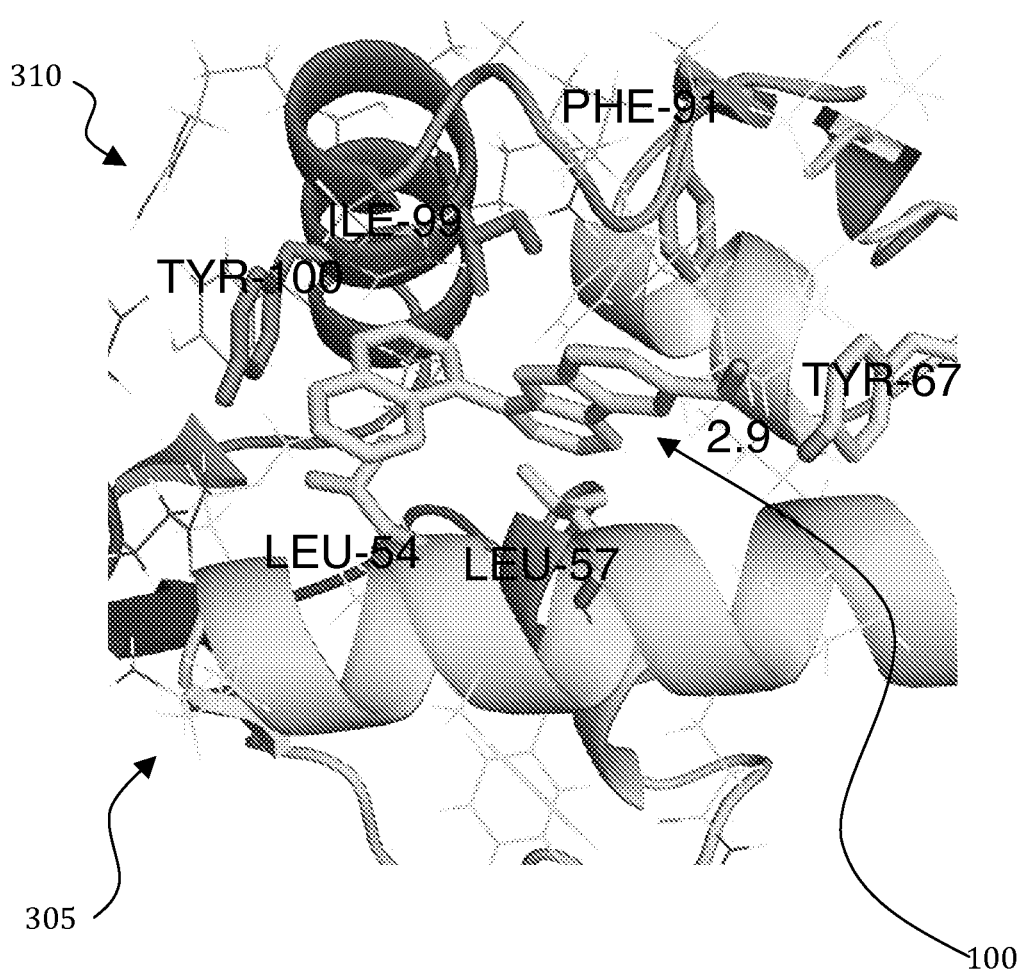
FIG. 3 illustrates a model of the interaction of SP-141 with MDM2, in accordance with an example embodiment.
Figure 4:
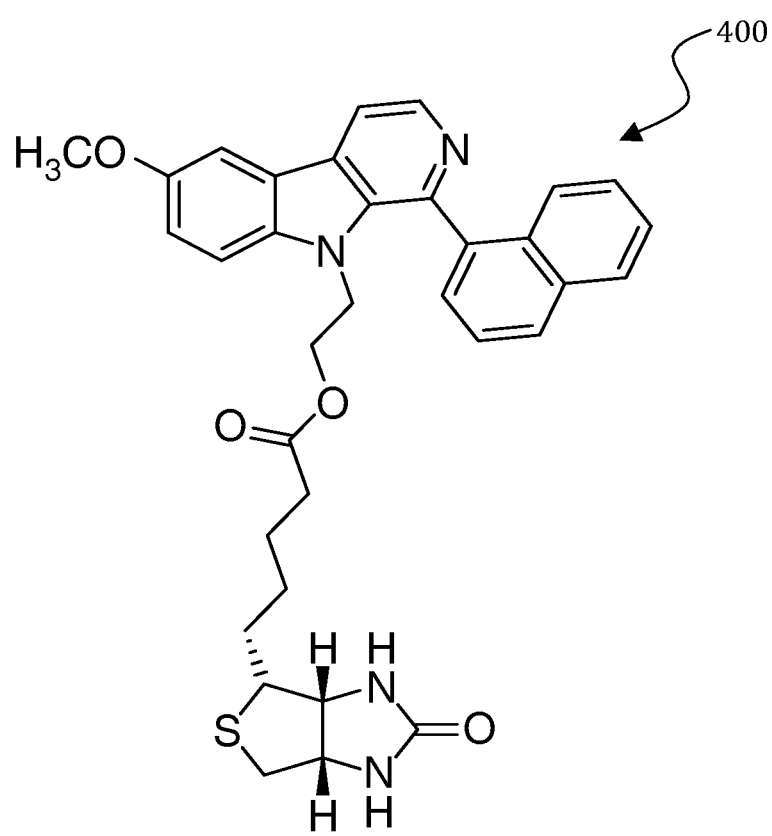
FIG. 4 illustrates the chemical structure of biotinylated SP-141, in accordancewith an example embodiment.

As illustrated in FIGS. 2 and 3. SP-141 can occupy the Leu26 pocket forming a hydrogen bond with Tyr-67. The naphthyl group of SP-141 can bind in the hydrophobic pocket occupied by Leu26 of p53, created by Leu54, lle99, Tyr100, and lle103 of MDM2. This can be confirmed using a biotin-SP-141 conjugate as shown in FIG. 4. It is noteworthy that compound SP-141 binds to MDM2, but not GST.

Figure 6:
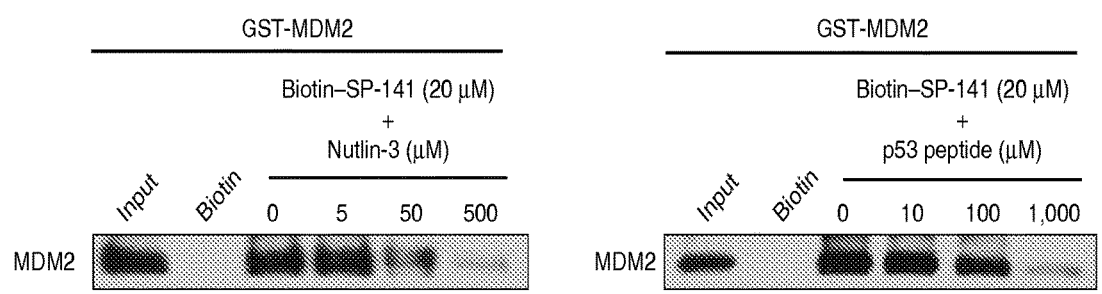
FIG. 6 illustrates a chart of experimental results, in accordance with an example embodiment.
Figure 8:
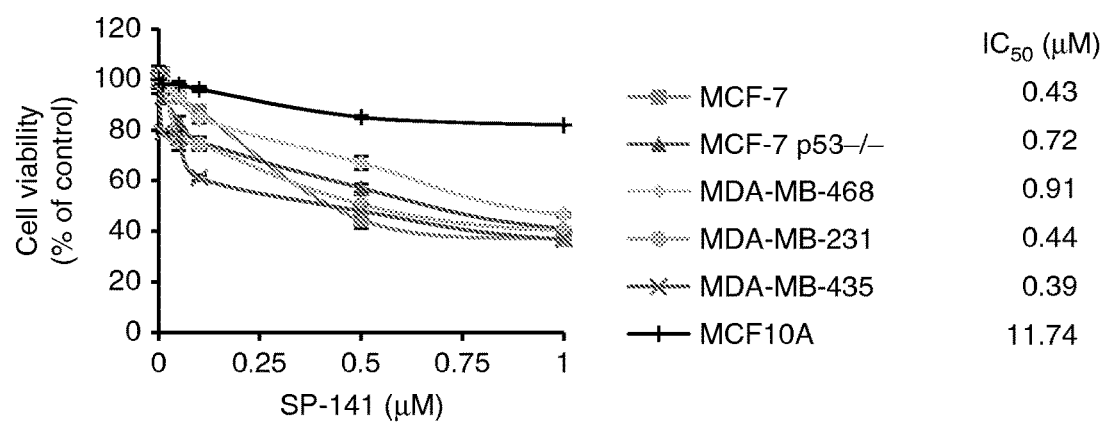
FIG. 8 illustrates a chart showing experimental results from cell exposure to SP-141, in accordance with an example embodiment.

Biotin-SP-141-MDM2 binding is also markedly reduced by Nutlin-3 and a nature p53 peptide. The reduction is proportional to dose. Thus, SP-141 can occupy the p53-binding site on MDM2 as illustrated by FIG. 6. Additionally, SP-141 binds to MDM2 with a Ki value of 28±6 nM, showing a significantly higher affinity than a nature p53 peptide (residues 16-27, Ki=1.11±0.19 mM) and nutlin-3 (Ki=45±4 nM). In a Biacore assay, SP-141 also showed a better binding affinity to the MDM2 protein (KD=43 nM) than the positive control, nutlin-3 (KD=90 nM). Thus, SP-141 serves as a specific MDM2 inhibitor with a high binding capacity for the MDM2 protein.

SP-141 also has cytotoxic effects on human breast, cancer cells. SP-141 effects on breast cancer cell viability can be tested in vitro using the 3-(4,5-dimethylthiazol-2-yl)-2,5-diphenyl tet-razolium bromide (MTT) assay. According to this assay, SP-141 can be effective with respect to multiple breast cancer cell lines representing different genetic backgrounds.

Figure 9:
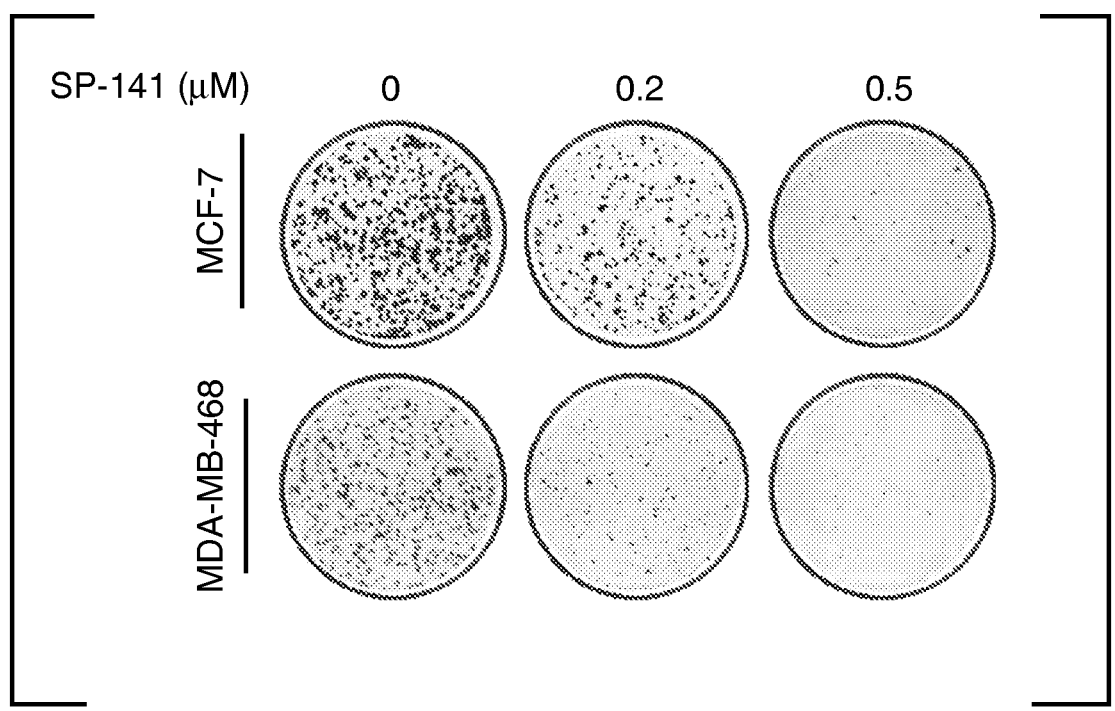
FIG. 9 illustrates a picture of experimental results of the colony formation assay, in accordance with an example embodiment.
Figure 10A:
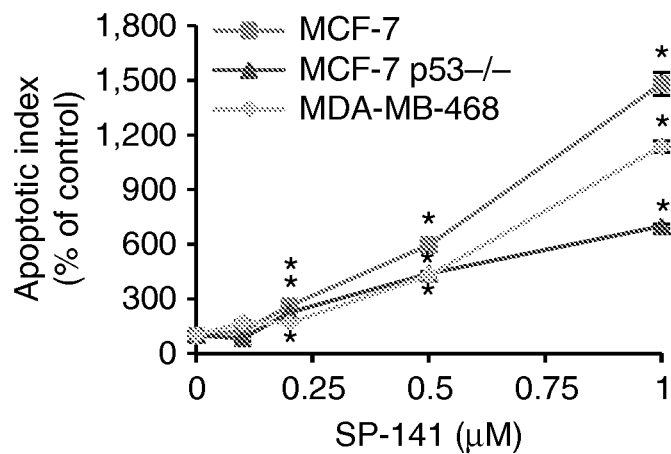
FIG. 10A illustrates a chart of experimental results associated with the apoptosis assay, in accordance with an example embodiment.

SP-141 can inhibit cancer cell colony formation in a concentration-dependent manner as shown in FIG. 9. For example as illustrated in FIG. 10A, three examined breast cancer cell lines experience a significant concentration-dependent increase (Po0.01) in apoptosis. In the p53 wt MCF-7, p53 KO MCF-7, and p53 mt MDA-MB-468 cells, a 1-mM concentration of SP-141 increased the apoptotic index 14-fold (Po 0.01), 7-fold (Po 0.01), and 11-fold (Po 0.01), respectively.

Figure 10B:
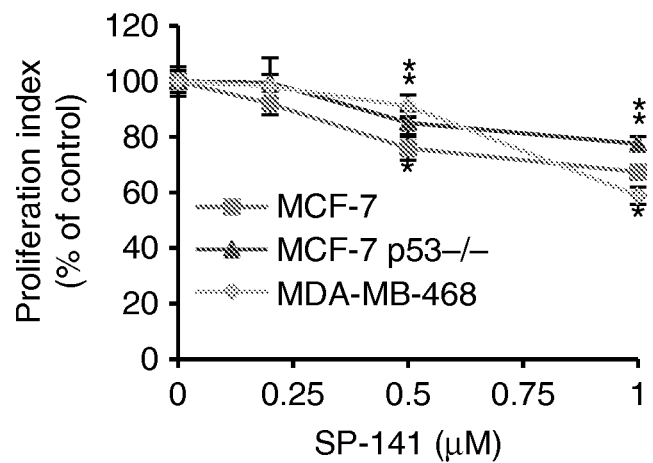
FIG. 10B illustrates a chart of experimental results associated with the proliferation assay, in accordance with an example embodiment.

SP-141 also inhibits cell proliferation as illustrated in FIG. 10B, in at least three human breast cancer cell lines. MDA-MB-468 cells are more sensitive to SP-141 treatment at higher concentrations than MCF-7 and MCF-7 p53 KD cells. However, MCF-7 cells (both p53 wt and p53 KD) are more sensitive to the lower concentrations of SP-141, with a 0.5-mM concentration leading to a significant decrease in proliferation (Po 0.01). SP-141 induces cell cycle arrest in the G2 phase at the 0.5 mM concentration (Po 0.01).

Figure 12:
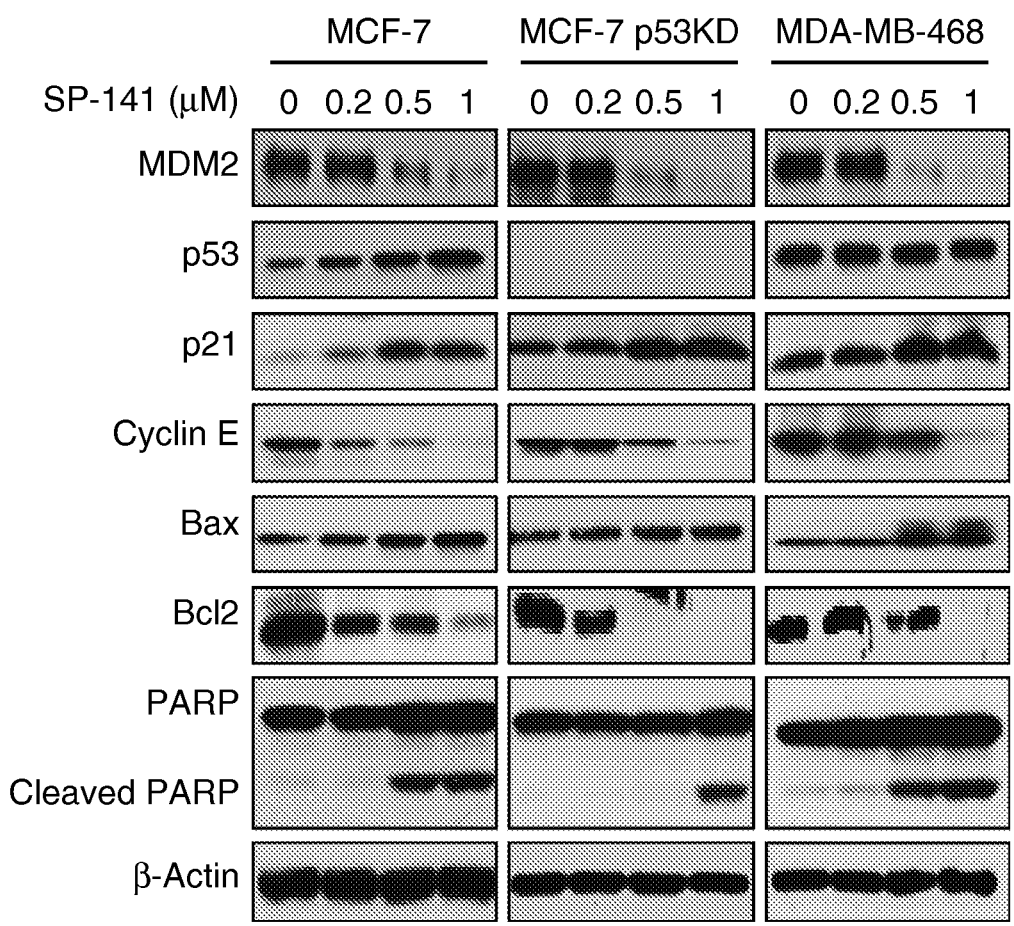
FIG. 12 illustrates a western blot analysis of the expression of MDM2 and proteins related to apoptosis and cell cycle arrest, in accordance with an example embodiment.

SP-141 also effects MDM2 expression. As shown in FIG. 12, the MDM2 protein levels decrease in a concentration-dependent manner in multiple tested cell lines. In the MCF-7 (p53 wt) cells, the wild-type p53 protein level increased, in accordance with an expected inhibition of MDM2. In addition, the expression level of p21Waf1/CIP1, an MDM2 target gene, suggests MDM2 inhibition. SP-141 increases the expression of cleaved PARP and Bax and decreases the expression of Bcl-2 and Cyclin E in a p53-independent manner.

Figure 13A:
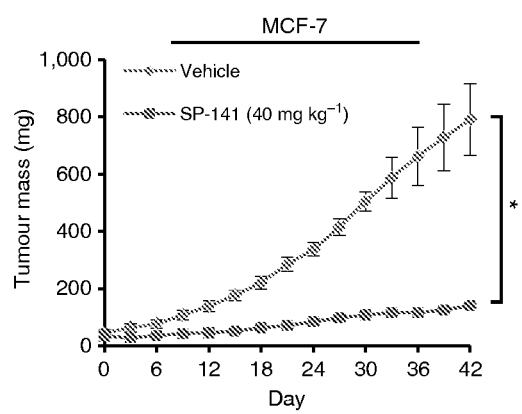
FIG. 13A illustrates a chart of tumor mass by day in mice bearing MCF-7, in accordance with an example embodiment.
Figure 13B:
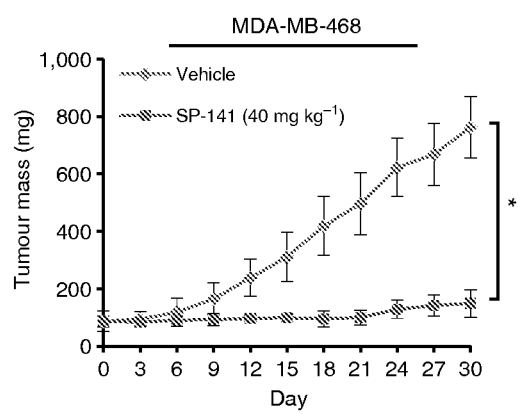
FIG. 13B illustrates a chart of tumor mass by day in mice bearing MDA-MB-468, in accordance with an example embodiment.
Figure 15A:
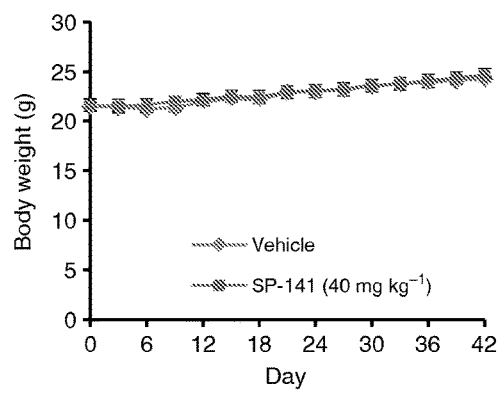
FIG. 15A illustrates a chart of bodyweight of animals treated with SP-141, in accordance with an example embodiment.
Figure 15B:
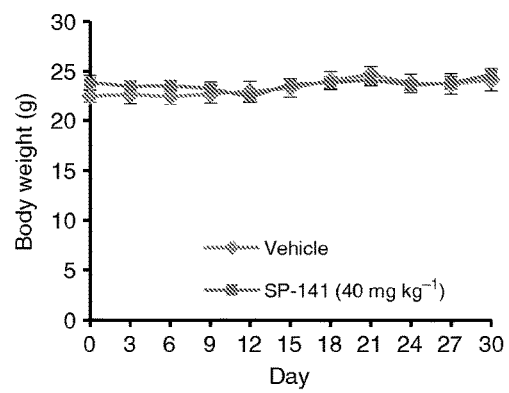
FIG. 15B illustrates a chart of bodyweight of animals treated with SP-141, in accordance with an example embodiment.
Figure 16:
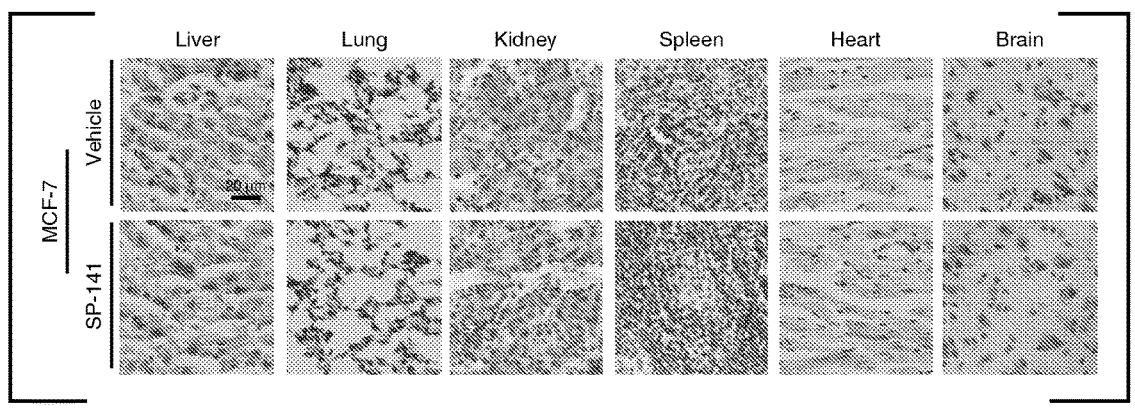
FIG. 16 illustrates a photograph of H&E staining of the paraffin sections of organs from mice bearing MCF-7 xenograft tumors, in accordance with an example embodiment.
Figure 18:
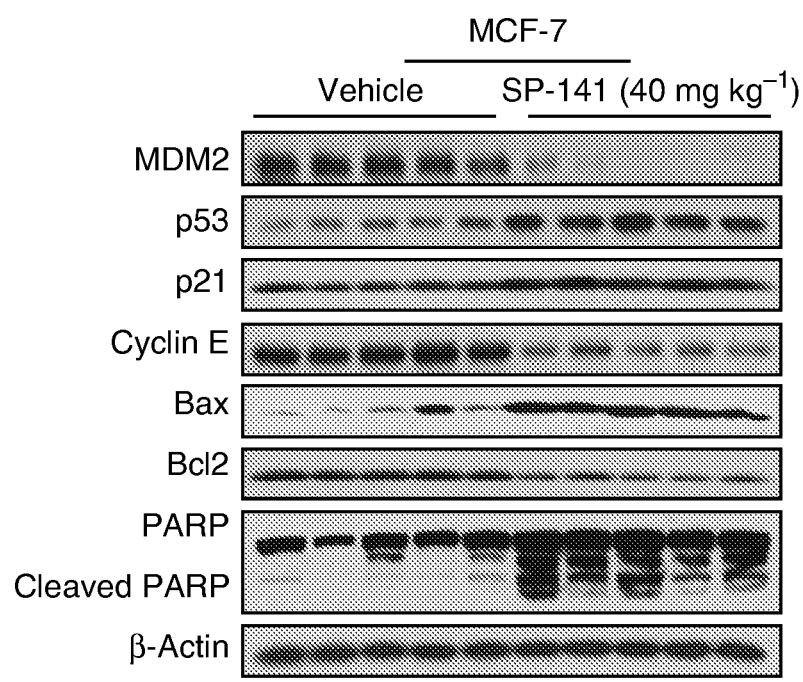
FIG. 18 illustrates a western blot of tumor samples, in accordance with an example embodiment.

SP-141 can also inhibit xenograft tumor growth in vivo. As evidence, SP-141 was administered to nude mice bearing MCF-7 and MDA-MB-468 xenograft tumors. SP-141 was administered by intraperitoneal (i.p.) injection at doses of 40 mg/kgn 1 per day for 42 and 30 days, respectively. As shown in FIGS. 13 and 14, SP-141 inhibits the MCF-7 and MDA-MB-468 xenograft tumor growth by 82% (Po 0.01) on day 42, and 80% (Po 0.01) on day 30. In addition, no significant host toxicity was observed at this dose in either model, as monitored by changes in body weight. Furthermore, there were also no gross organ (liver, lung, kidney, spleen, heart or brain) abnormalities at necropsy in the treatment group noted during histological examinations in the mice bearing MCF-7 xenograft tumors as shown by FIG. 18.

Figure 17:
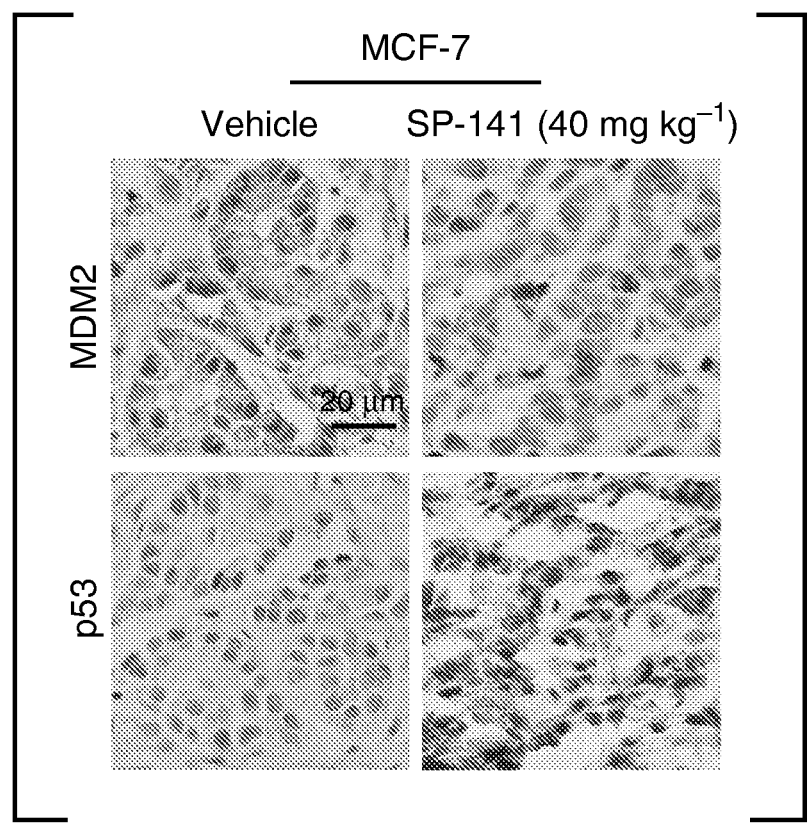
FIG. 17 illustrates a photograph of MCF-7 xenograft tumors removed from nude mice bearing MCF-7 and MDA-MB-468 xenograft tumors, in accordance with an example embodiment.

The molecular mechanisms underlying the effects of SP-141 can be verified by evaluating the expression levels of the various apoptosis and cell cycle-related proteins in vivo. As shown in FIG. 17, the protein levels of MDM2 are reduced and those of p53 are increased in the MCF-7 xenograft tumors, as determined with immunohistochemical staining. Western blot analyses, shown in FIG. 18, are consistent with the in vitro data; protein levels of MDM2 were decreased by SP-141, resulting in elevated expression of p53, p21, Bax, and cleaved PARP, and decreased expression of Cyclin E and Bcl-2. Similar results can be seen in the MDA-MB-468 xenograft model FIG. 19. Taken together, these data show that SP-141 effectively suppresses the growth of breast cancer xenograft tumors.

Figure 20:
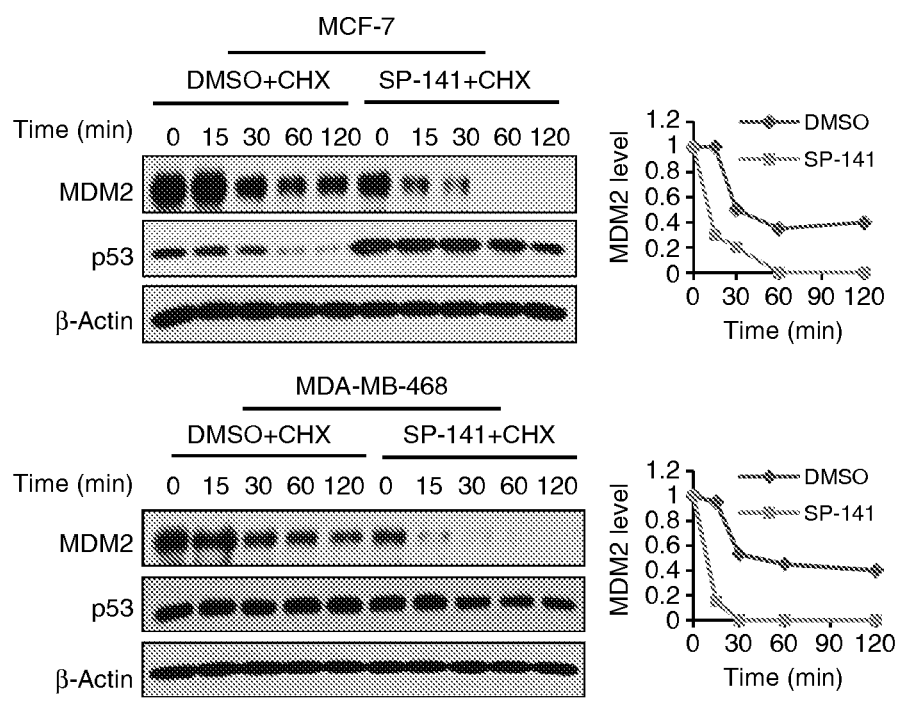
FIG. 20 illustrates a western blot analysis of MCF-7 and MDA-MB-468 cells treated with SP-141 (0.5 mM), and then exposed to cycloheximide (CHX, 15 mg ml 1), an inhibitor of protein synthesis, in accordance with an example embodiment.

SP-141 can also induce MDM2 protein degradation. Specifically. SP-141 can induce MDM2 inhibition in vitro and in vivo. As evidence, breast cancer cells treated with 0.5 mM of SP-141 or vehicle control for 24 hours, followed by exposure to the protein synthesis inhibitor, cycloheximide (15 mg ml 1) for various times increased the degradation rate of the MDM2 protein in both MCF-7 and MDA-MB-468 cells as shown in FIG. 20. The p53 protein was stabilized in MCF-7 cells, but not in the p53 mt MDA-MB-488 cells.

Figure 21:
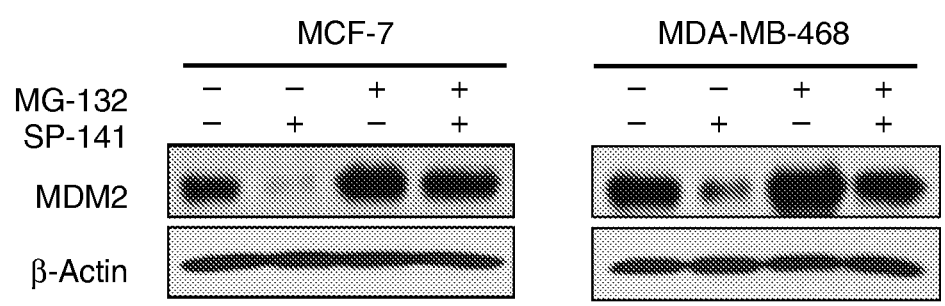
FIG. 21 illustrates a western blot analysis of the protein levels of MDM2 in cells treated with SP-141 (0.5 mM), and then were exposed to a proteasome inhibitor, MG 132, in accordance with an example embodiment.

In one example, breast cancer cells cart be treated with MG132 (25 mM), which is a proteasome inhibitor. This treatment reduces the effects of SP-141 on MDM2 as shown in FIG. 21, indicating that the SP-141-induced MDM2 degradation is proteasome-dependent. Co-treatment with MG132 also shows that SP-141 increases MDM2 ubiquitination.

Figure 23:
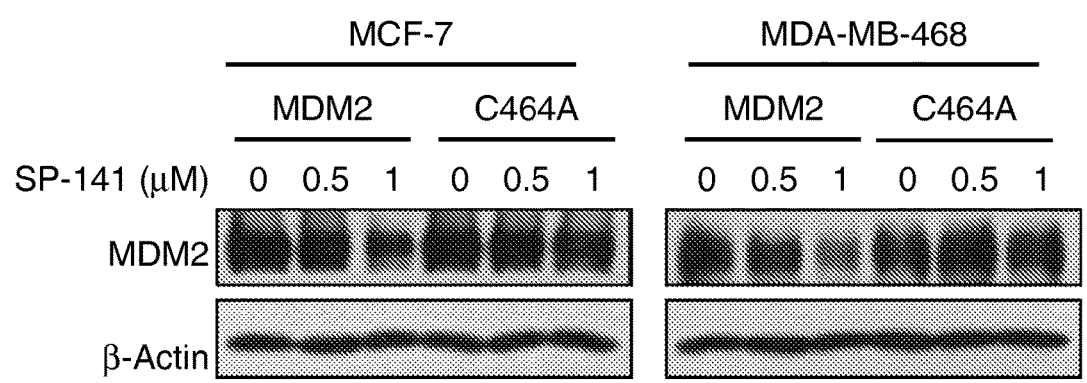
FIG. 23 illustrates a western blot analysis of cells transfected with a wild-type MDM2 plasmid or mutant MDM2 plasmid without E3 ligase activity (C464A), in accordance with an example embodiment.
Figure 24:
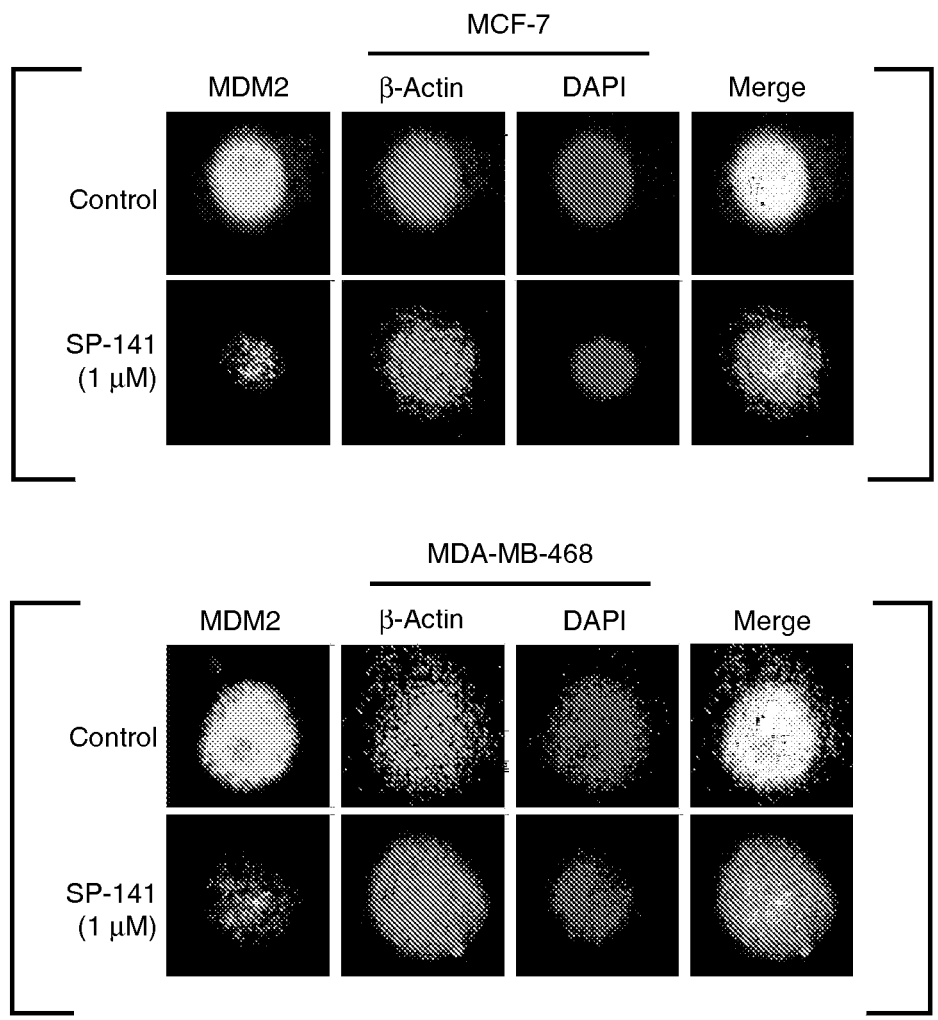
FIG. 24 illustrates a photograph of MDM2 immunofluorescence in control and SP-141 (1 mM)-treated cells, in accordance with an example embodiment.

MDM2 harbors a self-targeting E3 ubiquitin ligase, and its protein degradation is regulated by its autoubiquitination activity. SP-141 induces MDM2 autoubiquitination. To accomplish this, cells can be transfected with MDM2 or an MDM2 mutant (C464A) without E3 ubiquitin ligase activity. As shown in FIG. 23, the amount of wild-type MDM2 is decreased by SP-141, while the mutant MDM2 is resistant to the degradation induced by SP-141. The down regulation of MDM2 by SP-141 can be further confirmed by immunofluorescence. Compared with control cells, MDM2 staining is markedly decreased in SP-141-treated cells as shown in FIG. 24.

Figure 25:
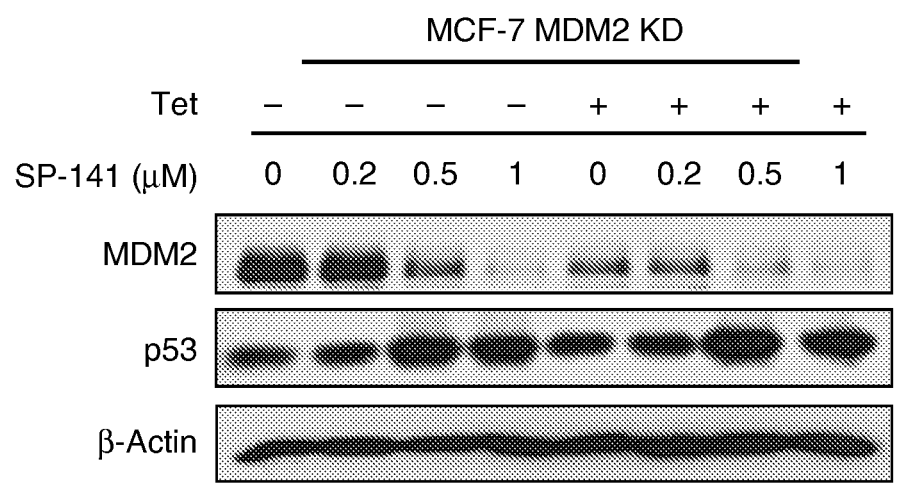
FIG. 25 illustrates a western blot analysis for the expression of proteins for inducible MDM2 KD MCF-7 cells that were incubated with (+Tet; 1 µgml$^{-1}$) or without (-Tet) tetracycline, in accordance with an example embodiment.
Figure 26:
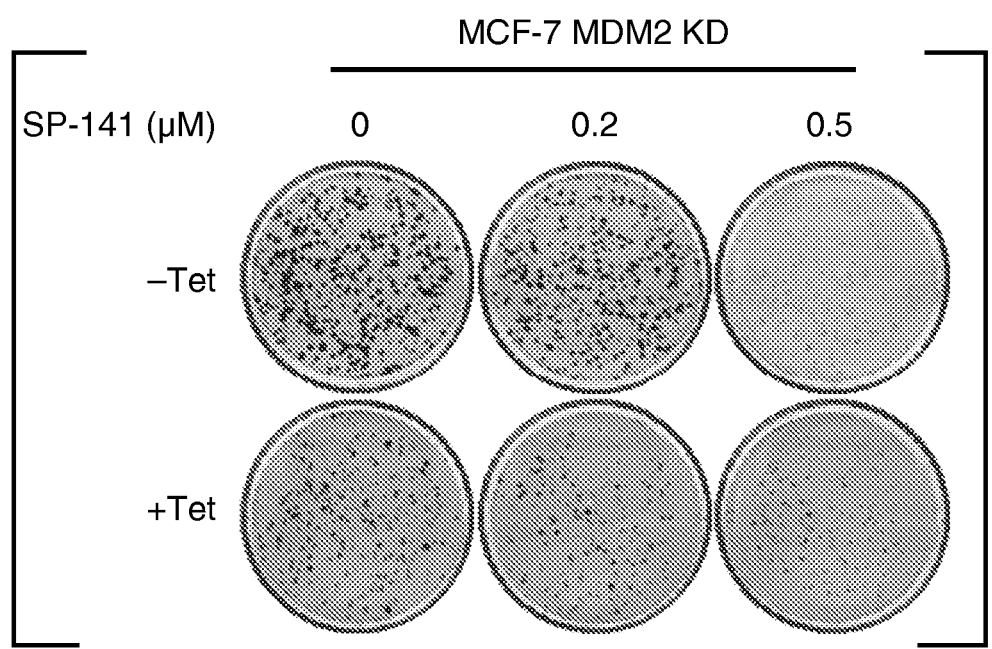
FIG. 26 illustrates a picture of experimental results of the colony formation assay, in accordance with an example embodiment.
Figure 27:
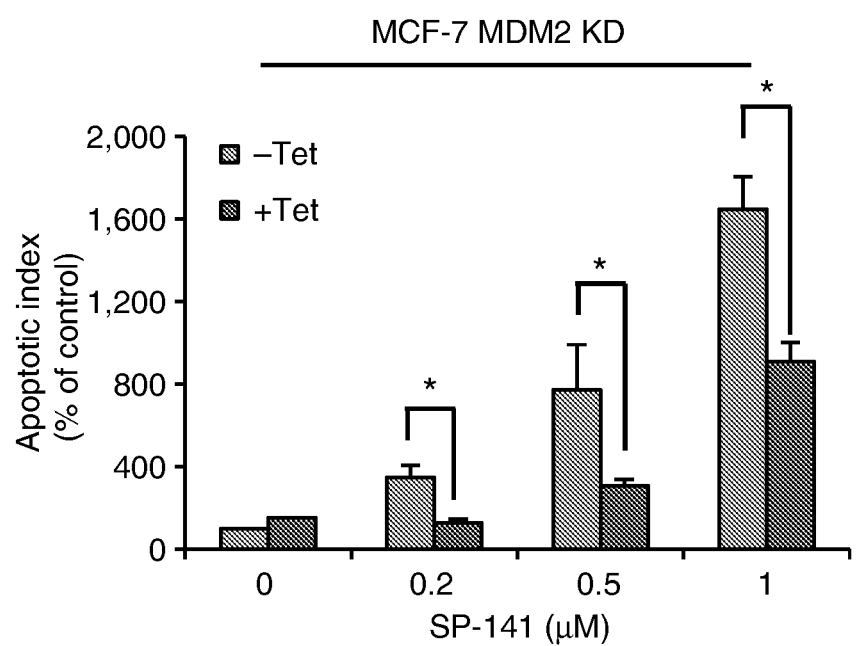
FIG. 27 illustrates a chart of an apoptosis assay, in accordance with an example embodiment.

MDM2 KD also blocks the inhibitory effects of SP-141. The anti-breast cancer activity of SP-141 is dependent on its effects on MDM2. For example, the effects of SP-141 on parent and inducible MDM2 KD MCF-7 cells can be investigated via Tet treatment. Tet treatment results in 79% KD of MDM2 protein expression as shown in FIG. 25. MDM2 KD itself inhibits colony formation as shown at FIG. 26, and increases apoptosis as shown at FIG. 27. After SP-141 treatment, compared with the parent cells, MDM2 KD reduces the effects of SP-141 on MDM2 protein degradation and reverses the cellular responses to SP-141 including the decrease in colony formation and increase in apoptosis. This shows MDM2 has a critical role in the SP-141-induced growth inhibition of breast cancer cells.

Figure 28:
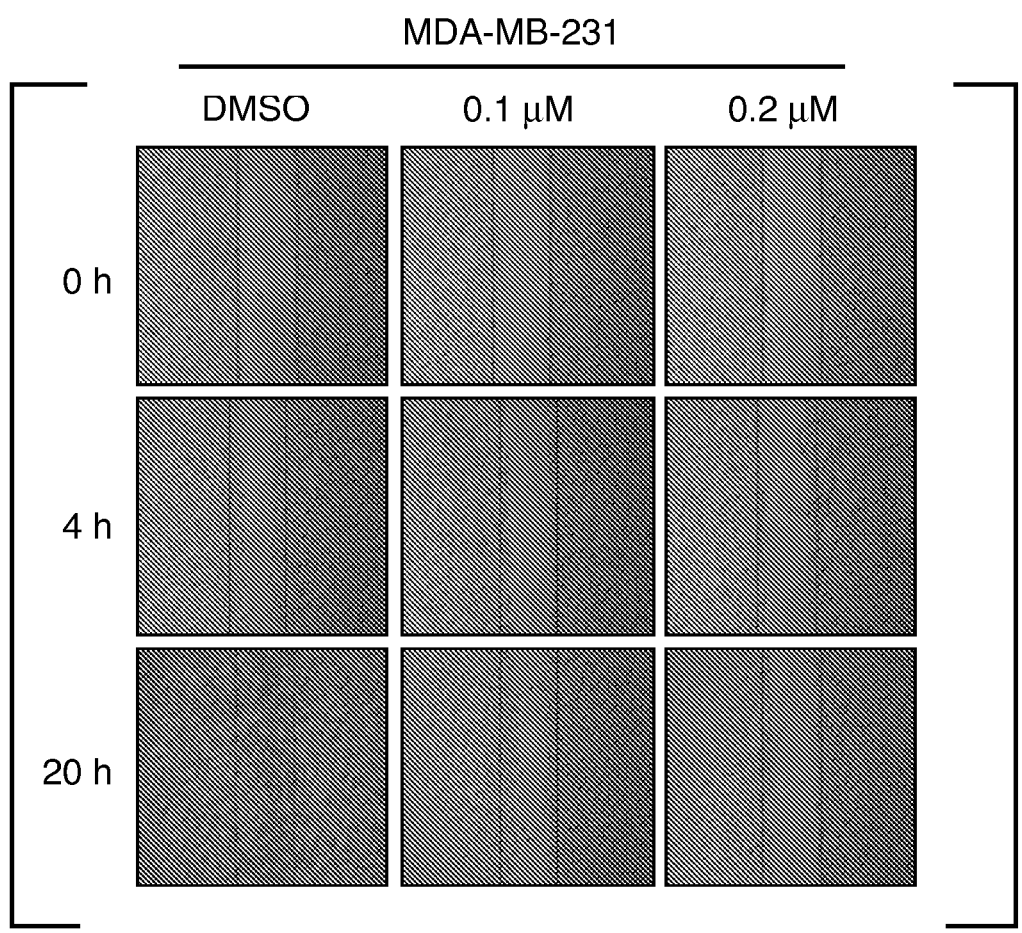
FIG. 28 illustrates a picture of cells in a six well-plate imaged at a selection of times in accordance with an example embodiment.

SP-141 inhibits cell migration in vitro and in vivo. A crucial component of tumor cell invasion is cell migration. A wound healing assay can be used to investigate the effect of SP-141 on cancer cell motility, using MDA-MB-231 human breast cancer cells. The cells can be treated with the vehicle, or with 0.1 or 0.2 mM of SP-141, in order to evaluate the cell migration into the wound made in the cell monolayer. As shown in FIG. 28, the control cells readily close the wound. Thus, the SP-141 treatment significantly decreased the cell migration in a concentration-dependent manner in various breast cancer cell lines.

Figure 29:
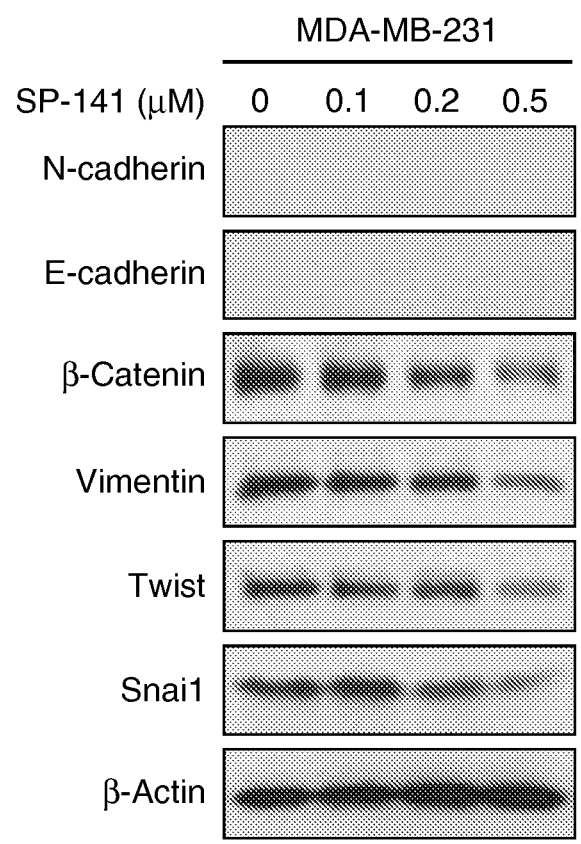
FIG. 29 illustrates a western blot analysis of the effects of SP-141 on the expression of EMT-related proteins in MDA-MB-231 cells in accordance with an example embodiment.

The epithelial-mesenchymal transition (EMT) is defined by the loss of epithelial characteristics and the acquisition of a mesenchymal phenotype. The EMT produces cancer cells that are invasive, migratory, and exhibit stem cell characteristics, hallmarks of cells that have metastatic potential. The treatment of the cells with SP-141 can result in a concentration-dependent decrease in the expression of b-catenin, vimentin, Twist, and Snail as shown at FIG. 29.

To validate the anti-metastatic effects of SP-141 in vivo, an experimental metastasis assay can be performed. MDA-MB-231-Luc breast cancer cells can be intravenously injected into a tail vein of nu/nu mice. The animals are randomly divided into a treatment group and a control group after cell injection. SP-141 can be administered by i.p injection at doses of 20 mg/kg, 1 per day for 2 weeks. The MDA-MB-231-Luc illumination signals in the lung tissues of control mice were significantly stronger than those in the SP-141 treated mice on days 8 and 15, indicating that the SP-141 treatment decreases the metastasis of breast cancer cells.

Turning specifically to the figures, FIGS. 1-7 illustrate that SP-141 directly binds to the MDM2 protein. In FIG. 1, the chemical structure 100 of SP-141 is shown. The binding site and orientation of SP-141 in the hydrophobic groove of MDM2 is illustrated in FIG. 2.

FIG. 3 illustrates a model of the interaction of SP-141 with MDM2. A cartoon illustration of MDM2 305 is illustrated while the residues in contact with SP-141 are rendered as sticks 310.

Figure 5:
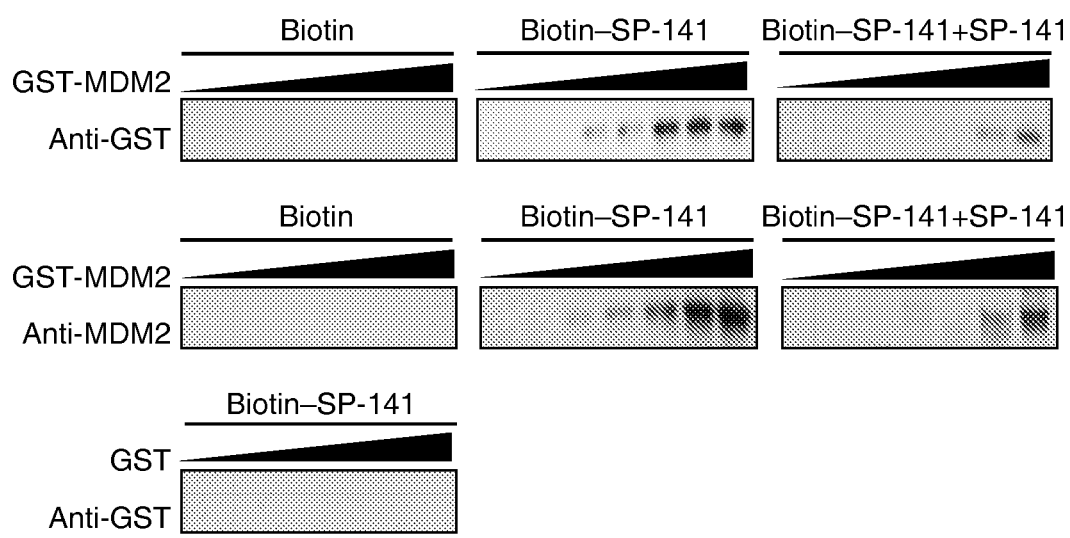
FIG. 5 illustrates a chart of experimental results, in accordance with an example embodiment.

The chemical structure 400 of biotinylated SP-141 is illustrated in FIG. 4 in accordance with another embodiment of the invention. A western blot analysis is illustrated in FIG. 5. This analysis is the result of an experiment wherein purified GST-MDM2 was incubated at various concentrations with biotinylated SP-141, which was then incubated with avidin beads in the presence or absence of 20 mM of non-biotinylated SP-141. Purified GST was used as a negative control. The bound protein was detected using anti-MDM2 and anti-GST antibodies.

FIG. 6 further illustrates a western blot analysis derived from an experiment wherein purified GST-MDM2 was incubated with biotinylated SP-141 (20 mM) that was incubated with avidin beads in the presence or the absence of Nutlin-3 (0, 5, 50, and 500 mM) and a natural p53 peptide (residues 16-27 0, 10, 100, and 1,000 mM). The bound protein was detected using anti-MDM2 antibody.

FIG. 7A illustrates a chart illustrating % inhibition. This is illustrative of competitive binding to recombinant human MDM2 proteins using an FP-based binding assay. Nutlin-3 and the natural p53 peptide were used as positive controls (mean±s.e.m.; n=9 for each data point). Similarly, FIG. 7B illustrates a chart or responses illustrative of competitive KD values of SP-141 to MDM2 as determined using the Biacore assay. The MDM2 protein was immobilized on a CM5 sensor chip. Nutlin-3 was used as a positive, control. It is noteworthy that all the assays were performed in triplicate, and all the experiments were repeated at least three times.

Figure 11:
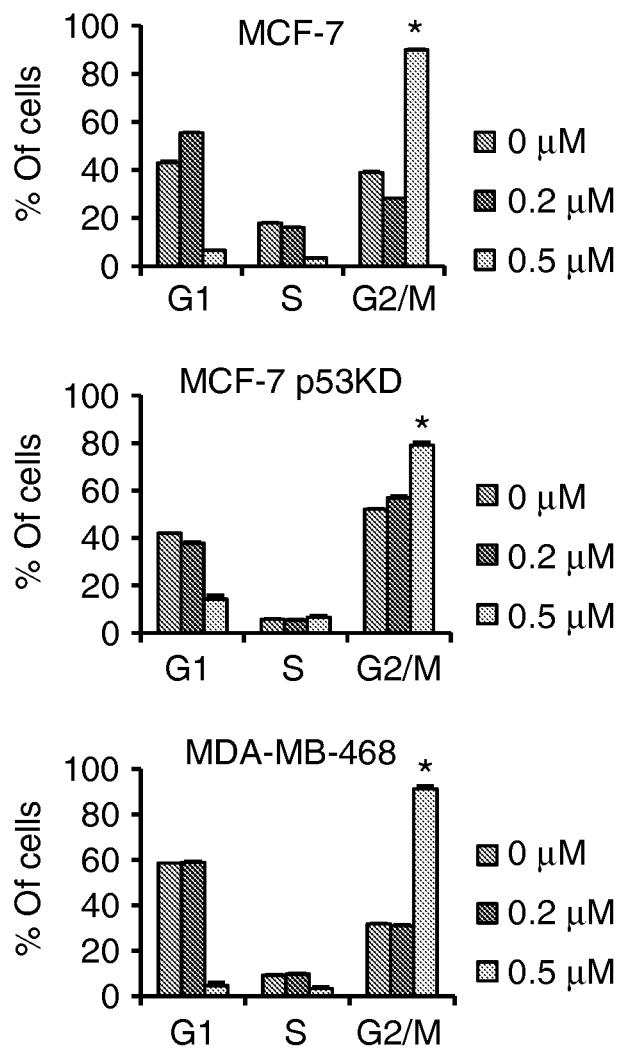
FIG. 11 illustrates a graph of experimental results associated with the cell cycle distribution assay, in accordance with an example embodiment.

FIGS. 8-12 are presented to illustrate that SP-141 induces breast cancer cell death. In experiments conducted by the inventors, cells were exposed to various concentrations of SP-141 for 72 hours, using the MTT assay to evaluate the cell viability and IC50 value. This is shown the chart provided in FIG. 8. FIG. 9 provides a photograph of such exposure for 24 hours using the colony formation assay. FIG. 10A illustrates a chart associated with 48 hours for the apoptosis assay and FIG. 10B illustrates a similar chart associated with 24 hours for the proliferation assay. FIG. 11 illustrates 24 hour for the cell cycle distribution assay. FIG. 12 illustrates a western blot analysis of the expression of MDM2 and proteins related to apoptosis and cell cycle arrest in human breast cancer cells. All these assays were performed in triplicate, and all the experiments were repeated at least three times (mean±s.e.m., n=9 for each data point, two-sided Student's t-test. *Po 0.01).

FIGS. 13-16 are presented to illustrate that. SP-141 suppresses breast xenograft tumor growth in vivo. FIGS. 13A and 13B illustrate tumor mass in nude mice bearing MCF-7 and MDA-MB-468, respectively. The xenograft tumors were treated with SP-141, which was administered by i.p. injection at 40 mg/kg 1 per day, 5 days per week for 42 and 30 days, respectively. FIGS. 14A and 14B illustrate the tumors after they were removed at the end of the experiments. The mice were also monitored for changes in body weight as a surrogate marker for toxicity in both the MCF-7 (as shown in FIG. 15A) and MDA-MB-468 (as shown if FIG. 15B) xenograft models. At the termination of the experiments, H&E staining of the paraffin sections of some organs from the mice bearing MCF-7 xenograft tumors was performed. Pictures of such sections are provided in FIG. 16 (scale bar, 20 mm). (Mean±s.e.m., n>10 for each data point, two-sided Student's t-test, *P<0.01).

Figure 19:
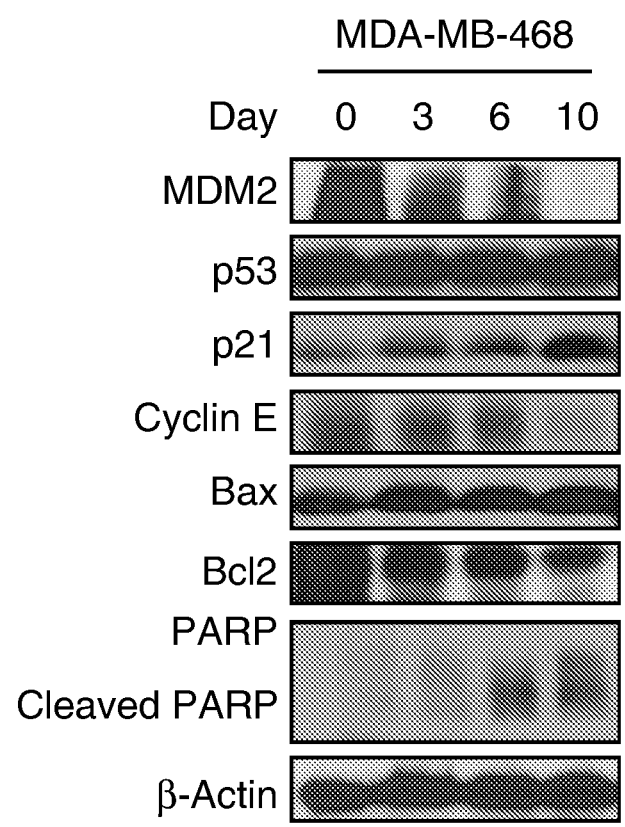
FIG. 19 illustrates a western blot of homogenized MDA-MB-468 xenograft tumors, in accordance with an example embodiment.

FIGS. 17-19 are provided to illustrate that SP-141 decreases the MDM2 expression in vivo. The inventors treated nude mice hearing MCF-7 and MDA-MB-468 xenograft tumors with SP-141, which was administered by i.p. injection at 40 mg kg 1 per day, 5 day per week for 42 and 30 days, respectively. At the end of the experiment. MCF-7 xenograft tumors were removed and further analyzed for their protein expression with immunohistochemistry as illustrated in the picture in FIG. 17 (scale bar, 20 mm). Western blotting as shown in FIG. 18 was also performed. Each lane in FIG. 17 represents a different tumor sample. On days 0, 3, 6, and 10, MDA-MB-468 xenograft tumors were homogenized and analyzed with western blot analysis, as shown in FIG. 19. All these experiments were repeated at least three times.

Figure 22:
FIG. 22 illustrates a western blot analysis of cells transfected with MDM2 and ubiquitin plasmids, followed by treatment with SP-141, in accordance with an example embodiment.

FIGS. 20-24 are presented to show that SP-141 destabilizes the MDM2 protein. MCF-7 and MDA-MB-468 cells were treated with SP-141 (0.5 mM), and then exposed to cycloheximide (CHX, 15 mg ml 1), an inhibitor of protein synthesis. The MDM2 protein levels were detected with western blot analysis, as shown in FIG. 20. The graphs in FIG. 20 show the quantification of the western blot data. Cells were treated with SP-141 (0.5 mM) for 24 hours, and then exposed to a proteasome inhibitor, MG 132 (25 mM), for an additional 6 hours. The protein levels of MDM2 were detected with western blot analysis, as illustrated in FIG. 21. Further, cells were transfected with MDM2 and ubiquitin plasmids, followed by treatment with SP-141 for 24 hours. The cells were then exposed to MG132 (25 mM) for an additional 6 hours, and the lysates were subjected to immunoprecipitation with an MDM2 antibody. The ubiquitinated MDM2 was detected using an antiubiquitin antibody, as shown in FIG. 22. Cells were transfected with a wild-type MDM2 plasmid or mutant MDM2 plasmid without E3 ligase activity (C464A). After treatment with SP-141 for 24 hours, MDM2 levels were detected with western blot analysis, as illustrated in FIG. 23. Representative images of MDM2 immunofluorescence in control and SP-141 (1 mM)-treated cells are illustrated in FIG. 24. B-actin and DAPI were used as internal references. All the experiments were repeated three times.

FIGS. 25-27 illustrate that MDM2 KD reduces the inhibitory effects of SP-141. Inducible MDM2 KD MCF-7 cells were incubated with (+Tet; 1 µgml$^{-1}$) and without (Tet) tetracycline for 24 hours, followed by exposure to various concentrations of SP-141 (0-1 mM) for various times. FIG. 25 provides a western blot analysis, the expression of proteins for 24 hours. FIG. 26 illustrates the colony formation assay after 24 hours. FIG. 27 shows the apoptosis assay after 48 hours. All assays were performed in triplicate, and all the experiments were repeated at least three times. (Mean±s.e.m., n=9 for each data point, two-sided Student's t-test, *P<0.01).

Figure 30:
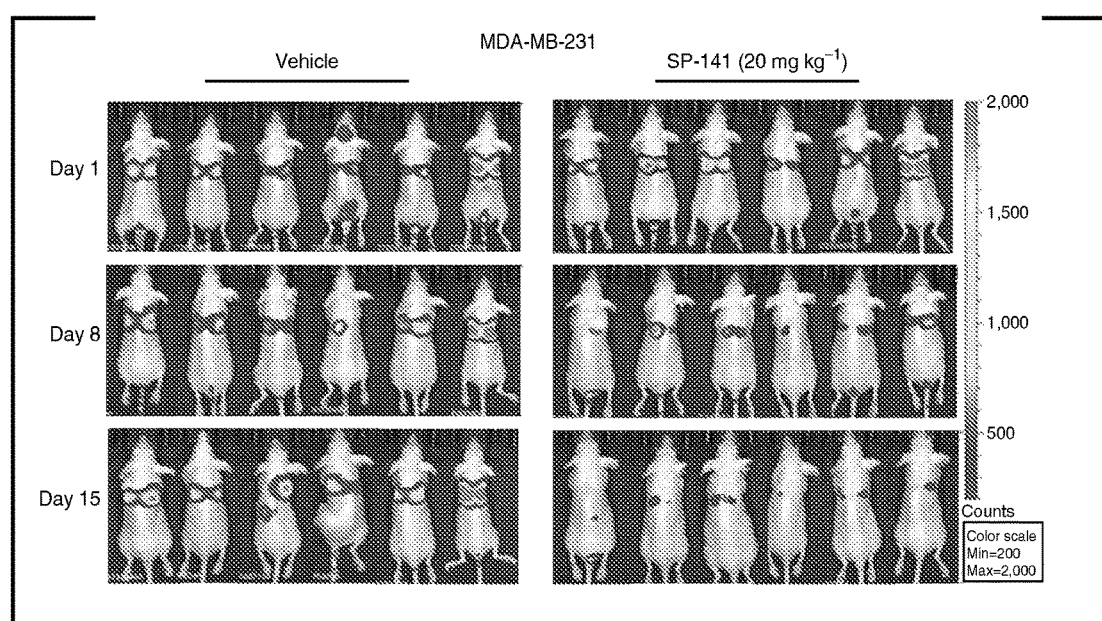
FIG. 30 illustrates a picture of luciferase signals in mice detected and photographed in vivo on days 1, 8, and 15, in accordance with an example embodiment.

FIGS. 28-30 are provided to illustrate that SP-141 inhibits cell metastasis in vitro and in vivo. MDA-MB-231 cells were grown to confluence in a six-well plate, illustrated in FIG. 28. A scratch was made at experimental time zero, and then the cells were exposed to various concentrations of SP-141. The wells were imaged at different time points. All the experiments were repeated at least three times. The effects of SP-141 on the expression of EMT-related proteins in MDA-MB-231 cells is shown in the western blot analysis provided in FIG. 29. About 1×10^6 MDA-MB-231-Luc cells were intravenously injected into a tail vein of nude mice. SP-141 was administered by i.p. injection at doses of 20 mg kg, 1 per day, 5 days per week for 2 weeks. The luciferase signals in the mice were detected and photographed using an MS in vivo image system on days 1, 8, and 15, as shown in FIG. 30.

In sum, SP-141 specifically binds to the MDM2 protein, based on the results from several assays, including the initial molecular docking, biotin-avidin pull-down assays, FP-based binding assay, and Biacore assay. SP-141 significantly decreases the growth of cancer cells with both wild-type (MCF-7) and non-functional (MCF-7 p53 KD, MDA-MB-468) p53, as well as oestrogen receptor-dependent (MCF-7) and independent (MDA-MB-468) cancer cells. SP-141 decreases the growth of both MCF-7 and MDA-MB-468 xenograft tumors. The down regulation of the MDM2 oncoprotein is responsible for the observed cytotoxic effects of SP-141.

SP-141 destabilized the MDM2 protein by promoting its autoubiquitination and proteasomal degradation, a unique molecular mechanism of action different from all of the existing MDM2 inhibitors.

MDM2 is the major target of SP-141. This can be verified using Tet-On tetracycline-inducible expression systems which confirm that KD of MDM2 resulted in the inhibition of cell growth and induction of apoptosis and that the MDM2 KD cells were resistant to the compound, showing less sensitivity in terms of the cell colony formation and apoptosis. The loss of sensitivity is due to the loss of molecular target (MDM2). This is indicative of the importance of MDM2 inhibition in the SP-141-induced anti-breast cancer activities. The SP-141-MDM2 complex is needed for SP-141s cytotoxicity against cancer cells.

In addition to its effects on the primary tumor, SP-141 also has anti-metastatic effects. SP-141 represses the migration of MDA-MB-231 cells. In addition, SP-141 treatment alters the expression levels of EMT-related proteins that are involved in crucial metastasis pathways, such as b-catenin, vimentin, Twist, and Snai1. SP-141 suppresses tumor metastasis through the inhibition of cell migration. Thus, SP-141 can inhibit tumor cell metastasis at least partly through its inhibition of MDM2 activity. SP-141 exerts its effects primarily by inhibiting cancer cell growth, colony formation, proliferation, cell cycle progression, and migration. SP-141 exerts these effects and also induces apoptosis by targeting MDM2, making use of both p53-dependent and independent, as well as ER-dependent and -independent pathways.

Based on the foregoing, it can be appreciated that a number of embodiments, preferred and alternative, are disclosed herein. For example, an SP-141 compound is a novel small molecule that can serve as a molecular-targeted chemotherapeutic agent. In one embodiment, a labeled compound has the structure shown in FIG. 1. The labeled compound can comprise SP-141 which comprises 6-methoxy-1-(naphthalen-1-yl)-9 H-pyrido[3,4-b]indole.

In one embodiment, the labeled compound inhibits expression of oncogenes. In another embodiment, the oncogene is Mouse Double Minute 2 protein. The compound can hind directly to Mouse Double Minute 2. In another embodiment, the labeled compound induces Mouse Double Minute 2 autoubiquitination and proteasomal degradation.

In another embodiment, the labeled compound inhibits cancer growth. The cancer growth can comprise breast cancer growth. In another embodiment, the labeled compound inhibits breast cancer growth in vivo. The labeled compound can inhibit breast cancer cell metastasis in vitro and in vivo.

It will be appreciated that variations of the above-disclosed and other features and functions, or alternatives thereof, may be desirably combined into many other different systems or applications. Also, it will be appreciated that various presently unforeseen or unanticipated alternatives, modifications, variations or improvements therein may be subsequently made by those skilled in the art which are also intended to be encompassed by the following claims.

What is claimed is:

1. A compound of the formula:

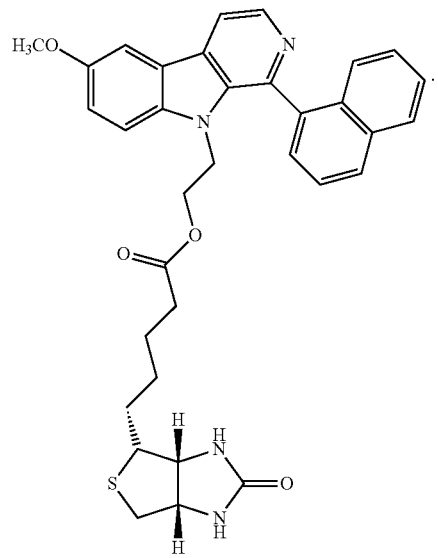

* * * * *